United States Patent [19]

Berg

[11] Patent Number: 5,039,380

[45] Date of Patent: Aug. 13, 1991

[54] SEPARATION OF M-XYLENE FROM P-XYLENE OR O-XYLENE BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 680,152

[22] Filed: Apr. 3, 1991

[51] Int. Cl.$^5$ .......................... B01D 3/36; C07C 7/00
[52] U.S. Cl. ..................... 203/60; 585/805; 585/866
[58] Field of Search ................ 203/60, 51; 585/805, 585/866

[56] References Cited

U.S. PATENT DOCUMENTS

| | | | |
|---|---|---|---|
| 2,456,561 | 12/1948 | Lake et al. | 203/60 |
| 2,763,604 | 9/1956 | Dorsey et al. | 203/60 |
| 2,957,811 | 10/1960 | Geiser | 203/60 |
| 3,227,632 | 1/1966 | Schmalenbach et al. | 263/58 |
| 3,684,665 | 8/1972 | Abe et al. | 203/60 |
| 4,488,937 | 12/1984 | Berg et al. | 203/60 |
| 4,676,875 | 6/1987 | Berg et al. | 585/808 |
| 4,738,755 | 4/1988 | Berg et al. | 203/60 |
| 4,822,947 | 4/1989 | Berg et al. | 203/58 |

*Primary Examiner*—Wilbur Bascomb, Jr.

[57] ABSTRACT m-Xylene is difficult to separate from p-xylene or o-xylene by conventional distillation or rectification because of the close proximity of their boiling points. m-Xylene can be readily separated from p-xylene or o-xylene by using azeotropic distillation in which the agent is an aliphatic ester. Typical examples of effective agents are: for m-xylene from p-xylene, propyl butyrate or methyl valerate; for m-xylene from o-xylene, hexyl formate or methyl valerate.

2 Claims, No Drawings

SEPARATION OF M-XYLENE FROM P-XYLENE OR O-XYLENE BY AZEOTROPIC DISTILLATION

FIELD OF THE INVENTION

This invention relates to a method for separating m-xylene from p-xylene and o-xylene using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

p-Xylene, B.P.=138.4° C. and m-xylene, B.P.=139.1° C. have a relative volatility of only 1.02 and are virually impossible to separate by conventional distillation or rectification. m-Xylene and o-xylene, B.P.=144.4° C. have a relative volatility of 1.12 and are difficult to separate rectification. Azeotropic distillation would be an attractive method of effecting the separation of xylenes if agents can be found that (1) will enhance the relative volatility between the xylenes and (2) are easy to recover from the xylenes.

The advantage of using azeotropic distillation in this separation can be seen from the data shown in Table 1 below.

TABLE 1

Theoretical and Actual Plates Required vs. Relative Volatility for Xylene Separation

| Relative Volatility | Theoretical Plates Required At Total Reflux, 95% Purity | Actual Plates Required, 75% Eff. |
|---|---|---|
| 1.12 | 52 | 70 |
| 1.20 | 33 | 44 |
| 1.25 | 27 | 36 |
| 1.30 | 23 | 31 |
| 1.35 | 20 | 27 |
| 1.40 | 18 | 24 |

The relative volatility of m-xylene to o-xylene is 1.12 and thus require 52 theoretical plates for separation by conventional rectification at total reflux. Plates possessing an efficiency of 75% are commonly employed and thus about 70 actual plates are required, clearly a difficult separation. One of the agents that I have discovered yields a relative volatility of 1.4 which would reduce the plate requirement to only 24.

The relative volatility of p-xylene to m-xylene is only 1.02 making this separation impossible by rectification. If an azeotropic distillation agent can be found that would increase the relative volatility to 1.4, p-xylene could be separated from m-xylene by rectification in a column with only 24 actual plates.

OBJECTIVE OF THE INVENTION

The objects of this invention are to provide a process or method of azeotropic distillation that will enhance the relative volatility of p-xylene to m-xylene and m-xylene to o-xylene in their separation in a rectification column. It is a further object of this invention to identify esters that are stable, can be readily separated from xylenes and can be recycled to the azeotropic distillation column with little decomposition.

SUMMARY OF THE INVENTION

The objects of the invention are provided by a process for the separation of p-xylene from m-xylene and m-xylene from o-xylene which entails the use of certain aliphatic esters as the agent in azeotropic distillation.

DETAILED DESCRIPTION OF THE INVENTION

I have discovered that propyl butyrate or methyl valerate will effectively increase the relative volatility between p-xylene and m-xylene and permit the separation of p-xylene from m-xylene by rectification when employed as the agent in azeotropic distillation. Table 2 summarizes the data obtained with these agents in a rectification column.

I have discovered that propyl butyrate, hexyl formate or methyl valerate will effectively increase the relative volatility between m-xylene and o-xylene when employed as the agent in azeotropic distillation. Table 3 summarizes the data obtained in a rectification column.

TABLE 2

Data From Runs Made In Rectification Column: p-Xylene From m-Xylene

| Agent | Column | Time hrs. | Weight % m-Xylene | Weight % p-Xylene | Relative Volatility |
|---|---|---|---|---|---|
| Propyl butyrate | Overhead | 1.5 | 51.4 | 48.6 | 1.124 |
|  | Bottoms |  | 30.9 | 69.1 |  |
| Methyl valerate | Overhead | 2 | 79.3 | 20.7 | 1.295 |
|  | Bottoms |  | 36.7 | 63.3 |  |
| " | Overhead | 7 | 85.6 | 14.4 | 1.38 |
|  | Bottoms |  | 35.9 | 64.1 |  |

TABLE 3

Data From Runs Made In Rectification Column m-Xylene From o-Xylene

| Agent | Column | Time hrs. | Weight % m-Xylene | Weight % o-Xylene | Relative Volatility |
|---|---|---|---|---|---|
| Propyl butyrate | Overhead | 3 | 64.3 | 35.7 | 1.176 |
|  | Bottoms |  | 35.5 | 64.5 |  |
| Hexyl formate | Overhead | 2 | 58.2 | 41.8 | 1.165 |
|  | Bottoms |  | 31.3 | 68.7 |  |
| " | Overhead | 5.5 | 55.3 | 44.7 | 1.175 |
|  | Bottoms |  | 27.8 | 72.2 |  |
| Methyl valerate | Overhead | 4 | 83.1 | 16.9 | 1.446 |
|  | Bottoms |  | 25.2 | 74.8 |  |
| " | Overhead | 10 | 79.6 | 20.4 | 1.40 |
|  | Bottoms |  | 25.4 | 74.6 |  |
| Isobutyl butyrate | Overhead | 2 | 62.5 | 37.5 | 1.20 |

TABLE 3-continued

Data From Runs Made In Rectification Column
m-Xylene From o-Xylene

| Agent | Column | Time hrs. | Weight % m-Xylene | Weight % o-Xylene | Relative Volatility |
|-------|--------|-----------|-------------------|-------------------|---------------------|
|       | Bottoms |          | 30.8              | 69.2              |                     |

THE USEFULNESS OF THE INVENTION

The usefulness or utility of this invention can be demonstrated by referring to the data presented in Tables 2 and 3. All of the successful agents show that m-xylene can be separated from p-xylene or o-xylene by means of azeotropic distillation in a rectification column and that the ease of separation as measured by relative volatility is considerable.

WORKING EXAMPLES

Example 1: Fifty grams of p-xylene, 70 grams of m-xylene and sixty grams of methyl valerate were charged to a glass perforated plate rectification column containing 7.3 theoretical plates. After two hours at total reflux, overhead and bottoms samples were taken and analysed by gas chromatography. The overhead was 79.3% p-xylene, 20.7% m-xylene; the bottoms was 36.7% p-xylene, 63.3% m-xylene which is a relative volatility of 1.295. After seven hours at total reflux, the overhead was 85.6% p-xylene, 14.4% m-xylene; the bottoms was 35.9% p-xylene, 64.1% m-xylene which is a relative volatility of 1.38 for this azeotropic mode of operation.

Example 2—150 ml. of m-xylene, 250 ml. of o-xylene and 150 ml. of methyl valerate were charged to a glass perforated plate rectification column containing 7.3 theoretical plates. After four hours at total reflux, overhead and bottoms samples were taken and analysed by gas chromatography. The overhead in the form of the m-xylene - methyl valerate azeotrope, was 83.1% m-xylene, 16.9% o-xylene; the bottoms was 25.2% m-xylene, 74.8% o-xylene which is a relative volatility of 1.446.

I claim:

1. A method for recovering p-xylene from a mixture of p-xylene and m-xylene which comprises distilling a mixture of p-xylene and m-xylene in the presence of an azeotrope forming agent, recovering the p-xylene and the azeotrope forming agent as overhead product and obtaining the m-xylene from the stillpot, wherein said azeotrope forming agent comprises propyl butyrate or methyl valerate.

2. A method for recovering m-xylene from a mixture of m-xylene and o-xylene which comprises distilling a mixture of m-xylene and o-xylene in the presence of an azeotrope forming agent, recovering the m-xylene and the azeotrope forming agent as overhead product and obtaining the o-xylene from the stillpot, wherein said azeotrope forming agent comprises a material selected from the group consisting of propyl butyrate, hexyl formate, methyl valerate and isobutyl butyrate.

* * * * *